US005616470A

United States Patent [19]

Ekramoddoullah et al.

[11] Patent Number: 5,616,470
[45] Date of Patent: Apr. 1, 1997

[54] **MONOCLONAL ANTIBODIES TO WHITE PINE BLISTER RUST FUNGUS *CRONARTIUM RIBICOLA***

[75] Inventors: Abul K. M. Ekramoddoullah; Douglas Taylor, both of Victoria, Canada

[73] Assignee: Her Majesty the Queen in right of Canada, as represented by the Minister of Natural Resources Canadian Forest Service, Ottawa, Canada

[21] Appl. No.: 594,034

[22] Filed: Jan. 30, 1996

[51] Int. Cl.$^6$ .......................... G01N 33/53; G01N 33/569

[52] U.S. Cl. .......................................... 435/7.31; 530/388.5

[58] Field of Search .................. 435/7.31, 33; 530/388.5

[56] References Cited

U.S. PATENT DOCUMENTS

| | | | |
|---|---|---|---|
| P.P. 5,918 | 3/1987 | Bauer | Plt./33 |
| 3,849,104 | 11/1974 | Daniel et al. | 504/117 |
| 4,845,197 | 1/1989 | Petersen et al. | 530/387 |
| 4,879,217 | 11/1989 | Petersen et al. | 435/7.31 |
| 5,187,064 | 2/1993 | Petersen et al. | 435/7.31 |
| 5,217,871 | 1/1993 | Petersen et al. | 435/7.31 |

*Primary Examiner*—James C. Housel
*Assistant Examiner*—Ginny Allen Portner
*Attorney, Agent, or Firm*—George A. Seaby

[57] ABSTRACT

White pine blister rust, which infects five-needle pines such as eastern white pine, western white pine and sugar pine, is caused by the fungus *Cronartium ribicola*. This invention provides monoclonal antibodies which recognize antigens of basidiospores of the fungus. The antifungal antibodies can be genetiacally incorporated into white pines to generate blister resistant trees.

3 Claims, No Drawings

MONOCLONAL ANTIBODIES TO WHITE PINE BLISTER RUST FUNGUS CRONARTIUM RIBICOLA

BACKGROUND OF THE INVENTION

1. Field of the Invention

This invention relates to monoclonal antibodies useful in the detection of the white pine blister rust fungus *Cronartium ribicola*.

2. Background of the Invention

White pine blister rust is a disease which infects five-needle pines such as eastern white pine, western white pine and sugar pine. The fungus was inadvertently introduced into western North America at Vancouver, Canada in 1910. The fungus has five different spore stages on two unrelated hosts, namely white pines and Ribes. The basidiospores are produced on Ribes in the Fall, and are transported by wind to pine foliage where they germinate. The mycelium of the fungus then grows down the needle until it reaches the bark causing the canker which eventually kills the tree. Although some larger and older trees can survive, infected young trees almost inevitably die.

Because western white pine trees have a high stumpage value and are resistant to root rot disease, a program has been developed in western Canada to select and screen blister rust resistant trees for planting seed orchards with the ultimate purpose of reforestation with resistant trees. Candidate trees, which are canker free, are identified, and seeds are collected from such trees. Two year old seedlings grown from the seeds are inoculated with the *Cronartium ribicola* fungus, usually in late August. In the following spring, the needle infection intensity is recorded. One hundred percent of high spotted seedlings develop cankers and are culled. Low spotted seedlings are kept for observation for as long as seven years, whereby some resistance characteristics such as no cankers or slow canker growth or needle shed are observed. Trees with such resistance mechanisms are eventually used in seed orchards.

Obviously, such a selection program based on phenotypic criteria is very time consuming and expensive, and may not be precise. Accordingly, a need exists for a method which facilitates the selection and screening of disease resistant trees.

SUMMARY OF THE INVENTION

An object of the present invention is to fill the above defined need by providing a method based on a biochemical marker for disease resistance.

A more specific object of the invention is to provide a hybridoma cell line which produces monoclonal antibodies which react specifically with the fungus *Cronartium ribicola*, Accordingly, the present invention relates to a hybridoma which produces a monoclonal antibody which reacts specifically with *Cronartium ribicola* wherein the hybridoma has the identifying characteristics of Mab 7 (ATCC HB-12029) or Mab 13 (ATCC HB-12030). The invention also relates to a monoclonal antibody produced by the hybridoma having the identifying characteristics of Mab 7 (ATCC HB-12029) or MAB 13 (ATCC HB-12030).

In accordance with another aspect, the invention relates to a method of detecting presence of the fungus *Cronartium ribicola* in a sample comprising the steps of contacting the sample with the monoclonal antibody which reacts specifically with *Cronartium ribicola*, and observing whether an antibody-antigen reaction occurs as a result of the presence of the *Cronartium ribicola* fungus.

In order to identify the desired biochemical markers, a detailed analysis of mechanisms underlying resistance to the rust is required. The availability of the markers also facilitates the genetic incorporation of specific resistance in trees; thus avoiding the risk of loosing other desirable genes as is possible in the present selection process outlined above. Specific antibodies to the pathogen are useful for distinguishing the origin of pathogenesis—related proteins, i.e. host or pathogen proteins. The antibodies are also needed for ultrastructural localization of the molecular components involved in the host-pathogen interaction. The antifungal antibodies can be genetically incorporated into white pines to generate blister resistant pine trees. The antibodies may also be useful in evaluating host resistance or susceptibility by immunochemically quantifying the fungal mass in an infected host.

DETAILED DESCRIPTION OF THE INVENTION

Production of Basidiospores

Defoliated black current (*Ribes nigrum L.*) plants were held at 4° C. for 3–4 months to eliminate possible contamination from powdery mildew and spider mites, and then placed in a growth chamber at 15° C. and a 12 hour photoperiod until leaf growth began. The conditions were then changed to a 16 hour photoperiod with 25° C. days and 20° C. nights. When there was sufficient foliage, the plants were inoculated with white pine blister aeciospores which had been collected from different cankers on mature western white pine at Lake Cowichan on Vancouver Island (British Columbia). The spores were dusted onto the underside of the leaves and the plants were misted with water, and a plastic bag placed over each plant for 24 hours. Urediniospores from the infected leaves were used to infect new leaves. When a sufficient level of infection occurred, growth chamber conditions were returned to 15° C. and a 12 hour photoperiod. Basidiospores produced on the infected leaves were collected over NaCl solution (1700 ppm) and harvested as described by Mathews & Miller (Mathews, F. R., and R. C. Miller, 1986, Concentrated Basidiospore Spray System for Inoculating While Pine with Blister Rust, pages 48–55 [Volume 1], Proceedings of the 18th IUFRO World Congress: Division 2 Forest Environment and Silviculture. Yugoslav IUFRO World Congress, Organizing Committee, Ljubljana, Yugoslavia). The basidiospores were frozen at −20° C., freeze dried, and checked for purity by scanning electron microscopy.

Extraction of Fungal and Conifer Foliage Proteins

Basidiospores of *C. ribicola* were suspended in cold acetone (precooled by adding dry ice) and homogenized for 5 minutes in a 5 ml tissue grinder (Canadawide Scientific Ottawa, Ontario, Canada). The solution was then vacuum filtered using a 0.45 μm filter in a Millipore vacuum filter flask (Millipore Canada Ltd., Toronto, Ontario, Canada). The basidiospore powder was allowed to dry and scraped into a scintillation vial and extracted with phosphate buffered saline (PBS; 0.54 g of $KH_2PO_4$, 2.14 g of $Na_2HPO_4$, 7.75 g of NaCl and made up to 1 l with distilled water pH 7.2) at 4° C. overnight and centrifuged at 10,000 g for 15 minutes at room temperature. The protein content of the supernatant, designated as PBS extract, was determined by Bradford's (Bradford, M. M., 1976, A Rapid and Sensitive Method for the Quantitation of Microgram Quantities of Protein Utilizing the Principle of Protein-dye Binding, Ann Biochem 73: 248–254) dye binding assay (Bio-Rad Protein Assay Kit, Bio-Rad Laboratories, Richmond, Calif., U.S.A.).

To extract fungal mycelia and conifer foliage proteins, fungal mycelia were obtained from cultures derived from single needle spots on sugar pine seedlings (Kinloch and Dupper, Manuscript submitted) while five collections of needles from western white pine were made. The first two collections were primary and secondary needles of healthy two year old plants and the other two were needles of mature western white pine infected with two fungi: *Scirrhia pini* Funk & Parker and *Rhizosphaera pini* (Corda) Maubl. (from Kootenay, British Columbia, Canada). The third one was needles from two year old seedlings infected with blister rust fungus. Fungal mycelia and conifer foliage were extracted with an extraction solution (ES) containing 4% SDS (sodium dodecyl sulfate), 5% mercaptoethanol and 5% sucrose according to the procedure described by Ekramoddoullah (Ekramoddoullah, A. K. M., 1991, Analysis of Proteins of Western White Pine [*Pinus monticola* Dougl.] Needles, pages 102–103 in Y. Hiratsuka, J. K. Samoil, P. V Blenis, P. E. Crane and B. L. Laishley, ads., Rusts of Pine Working Party Conference, Forestry Canada, Northwest Region, Northern Forestry Centre, Edmonton, Alberta, Information Report NOR-X-317; and 1993, Analysis Of Needle Proteins and N-terminal Amino Acid Sequences of Two Photosystem II Proteins of Western White Pine [*Pinus monticola* D. Don], Tree Physiol 12: 101–106). The protein content of the extract was determined using the method described by Ekramoddoullah and Davidson (Ekramoddoullah, A. K. M. and J. J. Davidson, 1995, A Method for the Determination of Conifer Foliage Protein Extracted Using Sodium Dodecyl Sulfate and Mercaptoethanol, Phytochem Anal 6: 20–24) using bovine serum albumin (BSA) as a standard.

Immunization of Mice

Four female BALB/c mice from University of Victoria Animal Care Unit, Victoria, British Columbia, Canada were immunized with PBS extract prepared from the basidiospores. Prior to immunization, pre-immune serum was collected from each mouse. Thereafter, each mouse received an initial intraperitoneal (i.p.) injection of PBS extract containing 100 μg protein antigen emulsified with Freund's Complete Adjuvant and four booster (4-week interval) injections of PBS extract containing 100 μg protein antigen in PBS. The antibody levels in the sera were monitored with ELISA as described hereinafter. The mouse with the best antibody titer (20,480) was boosted i.p. with 50 μg protein antigen in saline two days before removal of the spleen for cell fusion as described later.

Enzyme-linked Immunosorbent Assays (ELISA)

ELISA was performed with 96-well plates (Catalog No. 3590, Costar, Cambridge, Mass., U.S.A.) as described by Tan and Ekramoddoullah (Tan Y., and A. K. M. Ekramoddoullah, 1991, Immunochemical Characterization of the Entomopathogenic Fungus *Beauveria bassiana*, J Invertebr Pathol 57: 269–276) with the following modifications: Each well was coated with 5 μg of fungal protein and the ELISA plate was evaluated using a microplate reader (Model EL309, Bio-Tek Instruments Inc., Burlington, Vt., U.S.A.) interfaced with KineticCalc™ EIA application software (version 2.03, Bio-Tek).

Cell Fusion and Generation of Monoclonal Cell Lines

Hybridoma cell lines producing monoclonal antibodies (Mabs) to the white pine blister rust fungus were generated by fusing spleen cells of BALB/c mice immunized with basidiospore proteins with myeloma cells x63-Ag8.

Cell fusion was done as per Pearson et al (Pearson, T. W. et al, 1980, Methods for Derivation and Detection of Antiparasitic Monoclonal Antibodies, J Immunol Methods 34: 141–154) with the following modifications. A single cell suspension of the spleen was prepared in 2.5% fetal clone serum (FCS) (Hyclone Laboratories, Inc. Distributed by Professional Diagnostic Inc. Aurora, Ontario, Canada) in RPMI-1640 complete (RPMI1640, 1% sodium pyruvate, 1% L-glutamine, 1% gentamicin sulfate solution). For fusion, $1\times10^8$ spleen cells were pelleted with $2\times10^7$ myeloma cells, X63-Ag8. The cell mixture was incubated with 5% $CO_2$ at 37° C. overnight in a $CO_2$ water-jacketed incubator (Model Nu2700, NUAIRE, Plymouth, Minn.).

The cells were cloned in methylcellulose (Davis, et al, 1981, A Simple, Single Step Technique for Selecting and Cloning Hybridomas for the Production Of Monoclonal Antibodies, J Immunol Methods 50: 161–172). Cell supernatant was tested by ELISA for the presence of antibody. Clones secreting antibodies were recloned in methylcellulose followed by another recloning. Finally, hybridoma cells were frozen (in 90% FCS/10% dimethyl sulfoxide) and stored in liquid nitrogen (Cryogenic Tank, Model 35VHC, Union Carbide Corporation, Danbury, Conn., U.S.A.).

Gel Electrophoresis and Western Immunoblot

SDS polyacrylamide gel electrophoresis (PAGE) was carried out in the Protean slab cell apparatus (Bio-Rad, Richmond, Calif., U.S.A.) with 0.75 mm thick slab gels (12%) utilizing the Laemmli buffer system (Laemmli, U. K, 1970, Cleavage of Structural Proteins During the Assembly of the Head of Bacteriophage $T_4$, Nature 227: 680–685). Samples were appropriately diluted in extraction solution and boiled for 3 minutes prior to electrophoresis. Gels were stained with silver (Hochstrasser, D. F. et al, 1988, Methods for Increasing the Resolution of Two-dimensional Protein Electrophoresis, Ann Biochem 173: 424–435). Low molecular weight (range: 14.4–97.4 kDa) protein (Bio-Rad) and rainbow-colored protein (range: 14.3–200 kDa) standards (Amersham International plc, Amersham Place, England) were used to calibrate the gels and Western immunoblots.

For Western immunoblotting, proteins separated by SDS-PAGE were electrophoretically transferred (Towbin H. et al, 1979, Electrophoretic Transfer of Proteins from Polyacrylamide Gels to Nitrocellulose Sheets: Procedure And Some Applications, Proceedings of the National Academy of Sciences of the United States of America, 76: 4350–4354) from the gel onto immobilon-P membrane (Millipore Canada Ltd., Toronto, Ontario, Canada). Following transfer of the separated proteins, the membrane was blocked by incubating the membrane in gelatin [3% in TBS (Tris-buffered saline, 20 mM Tris-HC1, 500 mM CaCl, pH 7.5)]for 30 minutes at room temperature and was then washed with TBST (TBS containing 1% Tween 20™). The membrane was cut into 3-mm to 4-mm strips and incubated in screw-top culture tubes (16×150 mm, Canlab Division, Baxter Diagnostic Corporation, Mississauga, Ontario, Canada) with murine pre-immune sera and polyclonal anti-sera diluted 1:500 with 1 X superblocker (SB; 1 ml Tween-20 20 ml FCS, 20 ml glycerol, 36.03 g D-glucose made up to 200 ml with PBS, pH 7.4), or supernates of monoclonal cell lines diluted 1:1 with 2X SB overnight at 4° C. The membrane was finally processed for immunoblotting as described by Tan and Ekramoddoullah (supra). In some cases, the immunostained bands were quantified [Ekramoddoullah et al, 1995 (supra) J].

Isotyping of Monoclonal Antibodies

The mouse Typer Sub-Isotyping Kit (Bio-Rad) was used for identifying the mouse immuglobulin class and sub-class as outlined previously by Ekramoddoullah (Ekramoddoullah, A. K. M. et al, 1984, Determinants Of Ryegrass Pollen Cytochrome c Recognized By Human IgE And Murine Monoclonal Antibodies, Mol Immunol, 21: 375–382).

Basidiospores of White Pine Blister Rust Fungus and Production of Polyclonal Antibodies in Mice The examination of basidiospores with a scanning electron microscope indicated that the spores were devoid of extraneous materials. Proteins extracted from these spores were analyzed by SDS-PAGE which revealed that the extract contained at least 60 proteins having molecular mass ranging from 10–100 kDa. Mice were immunized with this extract resulting in good polyclonal antibody responses to these proteins. The antisera obtained from a mouse prior to the removal of the spleen for fusion was examined by Western immunoblot. As expected the antibodies present in the antisera reacted to a wide range of proteins present in the extract.

Derivation of Hybridoma Cell Lines Producing Monoclonal Antibodies

Cell fusion was performed using a spleen obtained from one hyperimmunized mouse. A total of 1284 hybridoma clones were obtained on initial screening by ELISA. Of these, the 18% that produced antibodies giving ELISA optical densities which were four times that of the background (i.e., wells not coated with WPBR antigen) were further selected and expanded. On repeated recloning of high-affinity antibody-producing clones, 22 stable clones were obtained. These cell lines were: 54, 96, 202, 283, 284, 287, 490, 504, 524, 542, 590, 696, 822, 823, 854, 856, 877, 903, 908, 993, 1000 and 1190 and the corresponding monoclonal antibodies (Mabs) secreted by them were designated as Mab1 to Mab22, respectively. The activity of these Mabs towards the various components present in the immunizing antigen of the basidiospores was determined by Western immunoblot. All but one of the monoclonal antibodies were shown to bind to more than one antigenic component of the basidiospores. Mab13 bound to a single antigenic component.

Isotypic analysis revealed that Mab12 was of $IgG_{2a}$ type carrying κ-light chains, while others were of the IgMκ type.

Determination of Specificity of Mabs

The Mabs were examined by Western immunoblot for non-specific reactivity to proteins derived from the primary needles of healthy two year old western white pine seedlings. Two Mabs (7 and 13) did not react with conifer proteins while others bound conifer proteins, indicating that the latter group of Mabs recognized epitopes common to proteins of both basidiospores and conifers. Similar results were obtained with secondary needles. The reactivity of these Mabs toward the proteins extracted from *S. pini* and *R. pini* Mabs 2, 6, 7, 12 and 13 did not react with proteins extracted from *S. pini* while others did. Mabs 1, 2, 6, 7, 10, 12 and 13 did not react with proteins extracted from *R. pini* while others did. Mabs 1 and 10 reacted with *S. pini* but failed to react with *R. pini*.

Reactivity of Mabs 7 and 13 to Fungal Mycelia and Blister Rust Infected White Pine Needles The reactivity of Mab7 and 13 to the mycelial proteins of the fungus is illustrated in Table 1.

TABLE 1

Reactivity of monoclonal antibodies to mycelial proteins of *Cronartium ribicola* as determined by Western-immunoblot

| | | Isolates[b] | | | | | | | | | | | |
|---|---|---|---|---|---|---|---|---|---|---|---|---|---|
| Mabs | Mr[a] | 44 | 45 | 66 | 67 | 85 | 86 | 116 | 117 | 123 | 124 | 230 | 233 |
| Mab7 | 65.9 | 0.333[3] | 0.388 | 0.311 | 0.325 | 0.345 | 0.413 | 0.441 | 0.362 | 0.354 | 0.405 | 0.220 | 0.149 |
| Mab13 | 60.7 | 0.110 | 0.194 | 0.182 | 0.209 | 0.176 | 0.163 | 0.175 | 0.150 | 0.206 | 0.214 | 0.186 | 0.122 |

[a]Molecular mass (kDa) of the mycelial antigens recognized by Mab
[b]cultures were derived from single needle spots on sugar pine inoculated with ribes leaves bearing telia from differing geographic locations: 44 & 45; Happy camp outplant site, CA: 66 & 67; Thompson Ridge, CA: 85 & 86; Nanaimo, B.C.: 116 & 117; Georgetown, CA: 123 & 124 Mountain Home, CA: 230; Virginia: 233; North Carolina
[c]Optical density of the immunostained band per 5 μg of protein of each isolate.

Two antigens (65.9 and 60.7 kDa) were detected in all 12 isolates. The quantity of these antigens varied among the isolates. These antigens were also detected by Western immunoblot in blister rust infected needles of western white pine seedlings.

SUMMARY

Thus, there has been described the production of Mabs which recognize antigens of basidiospores of the white pine blister rust fungus. The antigens were highly immunogenic as all mice gave a strong antibody response by producing antibodies to most antigens. Thus, from a single fusion, many monoclonal cell lines were obtained. However, after cloning and recloning, 22 stable cell lines were obtained which secreted high-affinity antibodies. The antibodies secreted by these clones were further examined by Western immunoblot to establish their specificity. Only two of the monoclonal cell lines produced antibodies which were highly specific to white pine blister rust fungal proteins. Twenty other Mabs showed varying reactivity towards the foliar proteins of western white pine. The reactivity of many Mabs towards conifer proteins was surprising in view of the fact that immunizing anitgens were obtained from clean basidiospores (i.e., basidiospores devoid of foliar or unrelated fungal materials). Since some fungal and conifer proteins (particularly glycoproteins) may possess common structural features, the antigenic cross-reactivity may be due to these common epitopes. Although endophytic fungi (Sieber-Canavesi, F. et al, 1993, Successional Patterns of Fungal Communities in Needles of European Silver Fir [*Abies alba* Mill.], New Phytol 125: 149–161) in two year old seedlings should be rare, the presence of these fungal proteins in conifer needles may also have contributed to the cross-reactivity. Consistent with the observed cross-reactivity of the Mabs, polyclonal antisera to WPBR basidiospores also reacted with proteins of white pine foliage (data not shown). Before the advent of Mabs, the cross-reacting antibodies from the polyclonal antisera would have been absorbed by affinity chromatography prepared with the cross-reacting antigen. In the present case affinity chromatography was not possible because the proteins of conifers can only be extracted with a high concentration of detergent (Ekramoddoullah, 1991 and 1993 above) not suitable for affinity chromatography. Although the immunizing antigen contained many antigenic components, the strategy used here was the differential screening of Mabs by Western immunoblot developed with immunizing antigen and cross-reacting antigens. Thus, the problems of antigenic cross-reactivity were circumvented by producing two specific Mabs. In addition to well defined specificity and affinity, the major advantage of Mabs is their unlimited supply now that hybridoma cell lines are available.

The cross-reactivity of the Mabs were also tested against two fungi which frequently infect white pine foliage (Funk, A, 1985, Foliar Fungi of Western Trees, Canadian Forestry Service, Pacific Forestry Centre, Victoria, B.C. Information Report BC-X-265). Most Mabs also bound to the fungal proteins to a varying degree. However, the two Mabs that did not react with white pine proteins also did not react with the fungal proteins. In addition, a third Mab did not bind the fungal proteins. The fact that Mab1 and 10 binds *S. pini* and *R. pini* suggests that these two Mabs could be used to distinguish these two fungi.

Deposits of pure hybridomas yielding Mabs 7 and 13 have been deposited with the American Type Culture Collection, Rockville, Md., and have been assigned accession numbers HB 12029 and HB 12029.

The embodiments of the invention in which an exclusive property or privilege is claimed are defined as follows:

1. A hybridoma which produces a monoclonal antibody which reacts specifically with *Cronartium ribicola* wherein the hybridoma is ATCC HB-12029 or ATCC HB-12030.

2. A monoclonal antibody produced by the hybridoma of claim 1.

3. A method of detecting presence of the fungus *Cronartium ribicola* in a sample comprising the steps of contacting the sample with the monoclonal antibody of claim 2, and observing whether an antibody-antigen reaction occurs as a result of the presence of the *Cronartium ribicola* fungus.

* * * * *